US006689351B1

(12) United States Patent
Pierce et al.

(10) Patent No.: US 6,689,351 B1
(45) Date of Patent: Feb. 10, 2004

(54) USE OF GM-CSF TO PROMOTE ACCELERATED WOUND HEALING

(75) Inventors: Glenn Pierce, Thousand Oaks, CA (US); Bruce W. Altrock, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 08/305,495

(22) Filed: Sep. 13, 1994

Related U.S. Application Data

(63) Continuation of application No. 07/821,498, filed on Jan. 21, 1992, now abandoned, which is a continuation of application No. 07/659,780, filed on Feb. 22, 1991, now abandoned.

(51) Int. Cl.$^7$ .............................................. A61K 38/18
(52) U.S. Cl. .............................. 424/85.1; 514/2; 514/8
(58) Field of Search ........................... 424/85.1; 514/8, 514/2, 21

(56) References Cited

U.S. PATENT DOCUMENTS

| | | | | |
|---|---|---|---|---|
| 4,929,442 A | * | 5/1990 | Powell | 424/85.2 |
| 4,950,483 A | * | 8/1990 | Ksander et al. | 424/422 |
| 5,110,604 A | * | 5/1992 | Chu et al. | 424/484 |

OTHER PUBLICATIONS

Hayward, *Plastic Surgery*, 1970, p. 621–23.*
*New York Times*, Mar. 28, 1989, p. 17, 20.*
Pruitt, *Army Inst Surgical Res Conf.*, Texas, 1988, p. 455.*
Schultz et al, *J Cell Biochem* 45, 1991, p. 346–52.*
Broadly et al, *Biotechnology Therapeutics* (1) 1989–90, p. 55–68.*
Greenhalgh et al, *Am J Pathol* 136(6) 1990, pp. 1235–1246.*
Ford et al, *Arch Surg* V(124) 1989, p. 1422–28.*
McGee et al. 1988, J. Surg. Res. 45:145–153.*
Bussolino et al. 1989. Nature 337:471–473.*
Hancock et al. 1988. J. Exp. Med. 168:1395–1402.*
Witmer–Pack et al. 1987. J. Exp. Med. 166:1484–1498.*
Clark et al. 1987. Science 236:1229–1237.*
Gough et al. 1985. EMBO J. 4:645–653.*
Groopman et al. 1989. New Engl. J. Med. 321:1449–1459.*
Ruef et al. 1990. Rev. Infect. Dis. 12:41–62.*
Dedhar et al. 1988. PNAS USA 85:9253–9257.*
Pruitt et al., U.S. Army Inst. of Surg. Res. Annual Research Progress Report for Fiscal Year 1988, pp. 112–121.
ten Dijke et al., Bio/Technology, 7:793–798 (1989).
Van Brunt, Bio/Technology, 7:15–16 (1989).

Broudy et al., Proc. Natl. Acad. Sci. USA vol. 83:7467:7471 (1986).
Burgess et al., Blood, vol. 69:43–51 (1987).
Cantrell et al., Proc. Natl. Acad. Sci. USA, vol. 82:6250–6254 (1985).
Chen et al., Blood, vol. 71:997–1002 (1988).
DeLamarter, John, Biochem. Pharm., vol. 37:3057–3062 (1988).
Diegelmann et al., Plast. Reconstr. Surg., vol. 68:107–113 (1981).
Eckersley et al., British Medical Bulletin, vol. 44:423–436 (1988).
Goslen, J.B., J. Dermatol. Surg. Oncol., vol. 9:959–972 (1988).
Gough et al., Nature, vol. 309:763–767 (1984).
Hermann et al., J. Clin. Invest., vol. 81:1415–1418 (1988).
Leibovich et al., Am. J. Pathol., vol. 78:71–100 (1975).
Metcalf et al., Esp. Hematol., vol. 15:1–9 (1987).
Munker et al., Nature, vol. 323:79–82 (1986).
Mustoe et al., Science, vol. 237:1333–1336 (1987).
Mustoe et al., Am. J. Surg., vol. 158:345–350 (1989).
Nicola et al., Proc. Natl. Acad. Sci. USA, vol. 81:3765–3769 (1984).
Paulsson et al., Nature, vol. 328:715–717 (1987).
Pierce et al., J. Cell. Biol., vol. 109:429–440 (1989).
Pierce et al., Proc. Natl. Acad. Sci. USA, vol. 86:2229–2233 (1989).
Rappolee et al., Science, vol. 24:708–712 (1988).
Ross et al., Cell, vol. 46:155–169 (1986).
Souza et al., Science, vol. 232:61–65 (1986).
Vadhan–Raj et al., New England J. of Med., vol. 317:1545–1552 (1987).
Wang et al., Immunology vol. 60:439–444 (1987).
Weisbart et al., Nature, vol. 314:361–363 (1985).
Welte et al., Proc. Natl. Acad. Sci. USA, vol. 82:1526–1530 (1985).
Zsebo, et al., Blood, vol. 71:99–103 (1988).
U.S. Army Inst. of Surg. Res., Annual Research Progress Report for Fiscal 1988, pp. 110–120(Phase II Study of Human Recombinant GM–CSF in Patients with Thermal Injury).

* cited by examiner

*Primary Examiner*—Elizabeth Kemmerer
(74) *Attorney, Agent, or Firm*—Amgen Inc.

(57) ABSTRACT

A method utilizing GM-CSF to promote accelerated wound healing in mammals is described. This method comprises administering topically to the mammal a therapeutically effective amount of this polypeptide. In addition, such methods comprising admixtures containing GM-CSF and at least one other protein are also disclosed.

12 Claims, 3 Drawing Sheets

USE OF GM-CSF TO PROMOTE ACCELERATED WOUND HEALING

This application is continuation of application U.S. Ser. No. 07/821,498, filed Jan. 21, 1992, now abandoned, which in turn is a continuation of application U.S. Ser. No. 07/659,780, filed Feb. 22, 1991, now abandoned.

FIELD OF THE INVENTION

The present invention relates generally to methods which enable the promotion of accelerated wound healing in patients who have suffered injury. Specifically, the present invention describes methods for promoting accelerated wound healing in patients suffering from a variety of wounds using the hematopoietic colony stimulating factor and GM-CSF.

BACKGROUND OF THE INVENTION

A. Wounds and Wound Healing

The human skin is composed of two distinct layers, the epidermis and dermis. Below these layers lies the subcutaneous tissue. The primary functions of these tissues are to provide protection, sensation, and thermoregulation to an animal. Secondarily, these layers protect the internal organs of the organism from shock or trauma by cushioning impacts from external forces and objects.

The outermost layer of skin, the epidermis, is approximately 0.04 mm thick, is avascular, is comprised of four cell types (keratinocytes, melanocytes, Langerhans cells, and Merkel cells), and is stratified into several epithelial cell layers [Leeson et al., (1985) Textbook of Histology, WB Saunders Co., Philadelphia]. The inner-most epithelial layer of the epidermis is the basement membrane, which is in direct contact with, and anchors the epidermis to, the dermis. All epithelial cell division occurring in skin takes place at the basement membrane. After cell division, the epithelial cells migrate towards the outer surface of the epidermis. During this migration, the cells undergo a process known as keratinization, whereby nuclei are lost and the cells are transformed into tough, flat, resistant non-living cells. Migration is completed when the cells reach the outermost epidermal structure, the stratum corneum, a dry, waterproof squamous cell layer which helps to prevent desiccation of the underlying tissue. This layer of dead epithelial cells is continuously being sloughed off and replaced by keratinized cells moving to the surface from the basement membrane. Because the epidermal epithelium is avascular, the basement membrane is dependent upon the dermis for its nutrient supply.

The dermis is a highly vascularized tissue layer supplying nutrients to the epidermis. In addition, the dermis contains nerve endings, lymphatics, collagen protein, and connective tissue. The dermis is approximately 0.5 mm thick and is composed predominantly of fibroblasts and macrophages. These cell types are largely responsible for the production and maintenance of collagen, the protein found in all animal connective tissue, including the skin. Collagen is primarily responsible for the skin's resilient, elastic nature. The subcutaneous tissue, found beneath the collagen-rich dermis, provides for skin mobility, insulation, calorie storage, and blood to the tissues above it.

Whenever there is an injury to the skin and/or the underlying soft tissue, a process to repair the resultant wound is immediately initiated in healthy organisms. In humans, this process does not lead to total regeneration of the injured outer integument unless the injury is confined to the epidermis and the basement membrane is left intact [Wokalek, H., (1988) CRC Critical Reviews in Biocompatibility, vol. 4, issue 3: 209–46]. Therefore, when a wound is characterized by more extensive tissue damage, the injured, destroyed, or lost tissue will not be reconstituted with like tissue, but will instead be replaced by scar tissue. Wounds characterized by tissue disruption penetrating completely through both the epidermis and dermis are known as full thickness wounds, while those which only extend through the epidermis but do not completely pass through the dermis are called partial thickness wounds.

The mechanisms of soft tissue injury can be divided into two general categories, mechanical and thermal. Mechanical forces are of three types, compression, shear, and tension. Compression, if enough force is applied, crushes the contacted tissue and produces serious wounds, such as those caused by blunt force trauma and gun shots. Wounds caused by shearing are the most common type of skin penetrating injury. Incisions, both surgical and nonsurgical, are examples of wounds produced by shearing forces. Because little energy is transferred to the surrounding tissue, little tissue devitalization occurs and healing is typically uncomplicated. Tension wounds occur when the skin is torn away from its subcutaneous base, either completely or leaving a flap with at least one edge still attached. The severity of a tension wound is dependent upon the amount of blood supply disruption to the flap and upon the size, thickness, and ratio of flap base width to flap length.

Thermal forces capable of producing wounds include cold, conduction, convection, electricity, and radiation. Generally, the severity of thermal wounds is dependent on the source, temperature, duration of exposure, and the ability of the skin to resist heat transfer [Trott, A. (1988) Ann. Emer. Med., vol 17: 1279–83].

Wound healing is the process through which the repair of damaged tissue(s) is accomplished. Wounds in which there is little or no tissue loss are said to heal by first or primary intention, while deep wounds suffering tissue loss heal by second or secondary intention. The wound healing process is comprised of three different stages, referred to as inflammation, granulation tissue formation, and matrix formation and remodeling [Ten Dijke et al., (1989) Biotechnology, vol. 7: 793–98].

The inflammatory response to soft tissue injury is initiated immediately upon infliction of the wound as tissue edges are separated and blood spills into the wound, activating the clotting cascade which leads to hemostasis. Initially there is a short phase of vasodilation in tissues surrounding the wound site followed by vasoconstriction. Platelets present in the wound, which aggregate to form the clot, also release a number of vasoactive compounds, chemoattractants, and growth factors [Goslen, J. B., (1988) J. Dermatol. Surg. Onco., vol 9: 959–72]. The clot itself is critical for eventual wound repair, as the provisional fibronectin matrix is used by fibroblasts and epithelial cells for ingress into the wound. Additionally, capillary permeability peripheral to the wound is increased, and because of the reduced blood flow, polymorphonuclear leukocytes (PMNs) adhere to the capillary walls and migrate into the wound, as do monocytes [Eckersley et al., (1988) British Medical Bulletin, vol. 44, No. 2: 423–36].

PMNS, such as neutrophils, are the predominant cell type found in the wound initially. PMNs and macrophages begin the process of cleaning the wound. This cleansing process is accomplished mostly through the phagocytosis of devitalized tissue and other debris. By days 3–5 post-injury, PMNs have largely been replaced by macrophages, which continue to remove dead and foreign material. In 1972, Simpson and Ross [J. Clin. Invest., vol 51: 2009–23] showed that an almost total absence of PMNs in the wound site did not inhibit wound healing. However, the role of macrophages in wound repair may be critical [Diegelmann et al., (1981) Plast. Reconstr. Surg., vol. 68: 107–113]. In experimental monocytopenic wounds, granulation tissue formation, fibroplasia, and collagen disposition are markedly impaired and healing is delayed [Leibovich et al., (1975) Am. J. Path., vol 78: 71–100; Mustoe et al., (1989) Am. J. Surg., vol 158: 345–50; Pierce et al., (1989) Proc. Nat. Acad. Sci. USA, vol. 86: 2229–33].

When found in wounds, macrophages are known to release a variety of biologically active substances that serve as chemoattractants for both monocytes and fibroblasts, such as transforming growth factor-β (TGF-β) and platelet-derived growth factor (PDGF) [Rappollee et al., (1988) Science, vol. 241: 708–12; Pierce et al., supra; Pierce et al., (1989) J. Cell Biol., vol. 109: 429–40]. See Obberghen-Schilling et al., (1988) J. Biol. Chem., vol. 263: 7741–46; Paulsson et al., (1987) Nature, vol. 328: 715–17; and Coffey et al., (1987) Nature, vol. 328: 817–20. Activated macrophages digest devitalized collagen and the fibrin clot. Dissolution of the clot allows the formation of granulation tissue in the wound site, the second wound healing phase.

Granulation tissue formation begins three to four days after the injury is inflicted and continues in the open wound until re-epithelialization has occurred. This stage is marked by the proliferation of fibroblasts and their migration into the wound site where they then produce an extracellular matrix, known as ground substance, comprised of collagen, fibronectin, and hyaluronic acid to replace the digested clot. This extracellular matrix serves as a scaffold upon which endothelial cells, fibroblasts, and macrophages are able to move. It is also utilized by myofibroblasts to promote wound closure by the process of wound contraction in full thickness wounds which heal by secondary intent.

Myofibroblasts are derived through the differentiation of resident fibroblasts shortly after a full thickness wound is inflicted. These myofibroblasts align radially using the newly deposited extracellular matrix and in an association with matrix, called the fibronexus, contract and promote more rapid wound closure [Singer et al., (1984) J. Cell Biol., vol. 98: 2091–2106].

In addition to wound closure, reepithelialization also occurs during this stage of wound healing. Epithelial cells proliferate at the wound edges and migrate across the ground substance. Epithelial cells can move only over viable, vascular tissue. Migration is halted by contact inhibition among epithelial cells, which at this point divide and differentiate to reconstitute the epithelium [Hunt et al., (1979) Fundamentals of wound management, Appleton-Century-Crofts].

As granulation tissue formation proceeds, angiogenesis, the formation of new blood vessels produced by endothelial cell division and migration, also occurs as the result of hypoxic conditions in the wound. Knighton et al. [(1983) Science, vol. 221: 1283–85] showed that macrophages, under hypoxic conditions, stimulate angiogenesis. The resultant increased vascularization increases blood flow and oxygenization in the wound. Eventually, as wound healing progresses into the matrix formation and remodeling phase, much of this newly formed vasculature regresses to leave a relatively avascular scar.

Collagen and matrix remodeling begin when granulation tissue formation begins and continues long after the wound has been covered by new epithelium and can continue for more than a year. This final stage of wound healing is characterized by devascularization and the replacement of granulation tissue and cells with a matrix comprised predominantly of type I collagen. This new relatively acellular, avascular tissue represents the scar. Scar formation primarily serves to restore tensile strength to the wounded tissue. However, the scar will not possess more than about 80% of the tensile strength which the tissue had prior to being injured.

Many factors can adversely affect the wound healing process, including the presence of necrotic debris, foreign material, infection, medication, and the age, health, and nutritional status of the injured individual. In addition, any process that impedes peripheral blood circulation, such as arteriosclerosis, prolonged pressure, varicose vein disease, and venous stasis, can adversely affect the delivery of oxygen, nutrients, chemical signals, and appropriate cell types to mediate healing in an injured patient, will impair wound healing.

Necrotic debris and foreign material typically are removed early in the healing process, first by washing the wound to remove macroscopic contaminants and then by endogenous PMNs and macrophages to remove remaining microscopic debris. Factors which inhibit cellular debridement retard wound healing. Such factors can include wound desiccation, medication, such as chemotherapy or steroids, and poor patient health and/or nutrition.

The physical condition of the patient is also important in wound healing. As age increases, the ability to repair injured tissue decreases, as the skin becomes thinner and the number of fibroblasts and amount of total skin collagen decrease [Shuster et al. (1975), Br. J. Dermatol., vol 93: 639–43]. Disease states such as alcoholism, anemia, diabetes, malnutrition, shock, and uremia lead to impaired oxygen and nutrient delivery to the wound site, thereby inhibiting the healing process. Also, diseases leading to monocytopenia can significantly impair wound healing.

Medications used to treat disorders can produce impaired wound healing. Chemotherapy, used to eliminate dividing cells in cancer patients, also suppresses the ability of such a patient to heal wounds, which is also dependent upon new cell growth. Steroids negatively impact all three phases of wound repair, inhibiting the initial inflammatory response, slowing the production of new epithelium and vascular tissue, and weakening the collagen matrix in the scar tissue [Bryant, R. (1987) J. Enterostomal Therapy, vol. 14, No. 6: 262–66].

Bacterial wound infection is the most common local cause for prolonged wound healing. Human skin is typically colonized by a number of microorganisms, including *Candida albicans, Staphylococcus epidermidis, Staphylococcus aureus,* and some Streptococcus strains. Thus, any wound which exposes underlying tissues to the environment becomes infected with at least resident microbial flora. Wounds which are well tended and in highly vascularized tissue resist infection, while those in ischemic tissue are much more susceptible to infection.

Blood flow and oxygen supply are necessary requirements for leukocyte-mediated bacterial cell killing. Leukocytes which phagocytose bacteria undergo a ten to twenty fold increase in oxygen consumption. Atmospheric $O_2$ is used for oxidative metabolism and to produce superoxide ions and hydrogen peroxide ($H_2O_2$), which are then used to kill internalized bacteria [Hunt, T., (1988) Annals of Emergency Medicine, vol 17: 1265–73]. Injuries having suboptimal oxygen perfusion are less able to dispose of contaminating microbes and therefore are at higher risk for the development of infection.

Factors additional to bacterial infection, medication, and physical condition of the patient can also lead to non-healing wounds. Certain partial and full thickness injuries, such as burns, skin grafts, and various types of ulcers, resist repair and produce significant pain and discomfort for the afflicted individual.

B. Colony Stimulating Factors

The human hematopoietic (blood forming) system replaces a variety of white blood cells (including neutrophils, macrophages, and basophils/mast cells), red blood cells (erythrocytes) and clot forming cells (megakaryocytes/platelets). The average human male's hematopoietic system has been estimated to produce on the order of $4.5 \times 10^{11}$ granulocytes and erythrocytes every year, which is equivalent to an annual replacement of total body weight [Dexter et al. (1985) BioEssays, vol. 2: 154–58].

CSFs are hormone-like glycoproteins which regulate hematopoiesis and are required for the clonal growth and maturation of normal hematopoietic precursor cells found in the bone marrow. These factors are produced by a number of tissues. Four CSFs isolated from human sources have been identified: granulocyte colony stimulating factor (G-CSF) [Welte et al., (1985) Proc. Nat. Acad. Sci. USA, vol. 82: 1526–30]; granulocyte-macrophage colony stimulating factor (GM-CSF) [Cantrell et al., (1985) Proc. Nat. Acad. Sci. USA, vol. 82: 6250–54]; macrophage colony stimulating factor (M-CSF); and multi-colony stimulating factor (multi-CSF, also referred to as Interleukin-3 [Nicola et al., (1984) Proc. Nat. Acad. Sci. USA, vol. 81: 3765–69], each accounting for the differentiation of particular immature progenitor cell types into mature cells. In addition, these factors are required for the maintenance of the mature cell types as well. In vitro, withdrawal of the appropriate CSF from culture leads to rapid degeneration of terminally differentiated hematopoietic cells dependent upon that CSF.

G-CSF is known to stimulate the production of predominantly neutrophil granulocytic colonies when used in vitro in the colony forming unit—granulocyte/macrophage (CFU-GM) assay. Other G-CSF activities have also been described. Currently, G-CSF in being studied for use in cancer treatment, both as a chemotherapeutic agent itself and as a compound capable of reducing the toxicity of other chemotherapeutic regimens.

Another therapeutically important colony stimulating factor is GM-CSF. This polypeptide is required continuously for the in vitro proliferation of macrophage and granulocytic progenitor cells. It also controls the irreversible commitment of these progenitors to form granulocytes and macrophages. Other biological activities may include regulation of the functional activity of the mature cell types [Gough et al., (1984) Nature, vol. 309: 763–67] and increasing chemotaxis towards recognized chemoattractants [Hematology, 4th ed., 1990, Williams et al., eds.]. Although GM-CSF acts on the same progenitor cell lineage as G-CSF, it also stimulates the production of monocytes, and thus may be useful in the treatment of monocytic disorders, such as monocytopenia.

For procedures describing the production of recombinant G-CSF (rG-CSF), see U.S. Pat. No. 4,810,643, hereby incorporated by reference. Procedures for the production of recombinant human GM-CSF have previously been described by Burgess et al. [(1987) Blood, vol. 69, No. 1: 43–51].

Therapeutic use of these recombinant proteins currently involves administration by the parenteral route, as the disease state to be treated is systemic or affects some internal tissue or organ which is not exposed. GM-CSF, when administered to patients by way of a peripheral vein, leads to phlebitis. Therefore, the preferred delivery mechanism is by central venous catheter. It has been found that daily subcutaneous injections of this cytokine are as effective in eliciting the desired response as is intravenous administration [Hematology, 4th ed., supra]. Doses of GM-CSF in excess of 32 $\mu$g/kg body weight/day, delivered by any route, are not well tolerated due to inflammatory reactions and pulmonary toxicity. Lower doses of GM-CSF therapy are generally well tolerated, but mild side effects typically include back pain, myalgia, chills, nausea, facial flushing, and fever.

G-CSF on the other hand produces significant neutrophilia without any appreciable side effects, except for the dose-limiting side effect of bone pain, which is believed to arise due to the expansion of granulocytic cells in the bone marrow. The maximum dose capable of being given by injection or venous catheter without producing this adverse effect is up to 60 $\mu$g/kg body weight/day.

In order to be used as a therapeutic agent and be administered by the parenteral route, recombinant proteins like G-CSF and GM-CSF are generally formulated into acceptable pharmaceutical preparations before being administered to patients. Such formulations typically involve the suspension of the biologically active material in an isotonic aqueous buffer adjusted to physiological pH. Such parenteral administration of the polypeptides discussed herein enables the stimulation and proliferation of cell types involved in wound healing and may thus constitute appropriate treatment in such situations.

C. Current Methods to Promote Wound Healing

Excluding infection or other complications, the normal wound healing process often results in the complete restoration of tissue function. Classically, the medical profession has been limited in what it can do to promote wound healing. In the past, such activities have been limited to the cleansing and debridement of the initial wound, suturing the wound or grafting skin if appropriate, dressing the wound to prevent desiccation and infection, and applying antibiotics, either locally or systemically, to reduce the risk of infection. Such treatment has been designed to provide optimal conditions for the natural healing process.

It has been noted that a number of recombinant growth factors may accelerate the wound healing process, in both acute and chronic wounds, in animal models. These recombinant derived factors include Platelet-Derived Growth Factor (PDGF), Fibroblast Growth Factor (FGF), Epidermal Growth Factor (EGF), and Transforming Growth Factors $\alpha$ and $\beta$ (TGF-$\alpha$ and TGF-$\beta$). Additionally, other recombinant growth factors, including insulin, Insulin-like Growth Factors I and II (IGF-I and IGF-II, respectively), Interferons (IFNs), Interleukins (ILs), KGF (Keratinocyte Growth Factor), Macrophage Colony Stimulating Factor (M-CSF), Platelet-Derived Endothelial Cell Growth Factor (PD-ECGF), and Stem Cell Factor (SCF), may promote the activation, proliferation, and/or stimulation of cell types involved in the wound healing process.

EGF is a polypeptide growth factor (the mature, processed form is 53 amino acids in length [Gray et al., (1983) Nature, vol. 303: 722–25]). In humans, this protein inhibits gastric acid secretion while murine EGF is known to be mitogenic for a number of cell types, including endothelial, epithelial, and fibroblastic cells [Nakagawa et al., (1985) Differentiation, vol. 29: 284–88].

FGF comprises a family of single chain proteins 14–18kD in size which tightly bind the potent anticoagulant heparin. Two FGF types, acidic and basic, have been reported. The 146 amino acid basic form (bFGF) is more stable and ten times more potent in stimulating mesodermal cells, such as fibroblasts, endothelial cells, and keratinocytes, than acidic FGF (aFGF). See Esch et al., (1985) Proc. Nat. Acad. Sci. USA, vol. 85: 6507–11].

Insulin is a protein hormone secreted by the cells of the pancreatic islets. It is secreted in response to elevated blood levels of glucose, amino acids, fatty acids, and ketone bodies, promoting their efficient storage and use as cellular fuel by modulating the transport of metabolites and ions across cell membranes and by regulating various intracellular biosynthetic pathways. Insulin promotes the entry of glucose, fatty acids, and amino acids into cells. Additionally, it promotes glycogen, protein, and lipid synthesis while inhibiting glucogenesis, glycogen degradation, protein catabolism, and lipolysis. Insulin consists of α and β subunits linked by two disulfide bridges.

IGF-I an IGF-II are members of a growth hormone-dependent family which mediate the effects of growth hormones. These proteins are known to be important in the regulation of skeletal growth. Both molecules have close structural homology to insulin and possess similar biological activities. IGF-I shares a 43% amino acid sequence homology with proinsulin, while IGF-II shares 60% homology with IGF-I. The IGFs are somewhat unique as compared to the other proteins described herein, in that there is essentially no detectable free IGF species present in the blood plasma of mammals. Instead, the IGFs are bound to specific carrier plasma proteins of higher molecular weight [Ooi et al., (1988) J. Endocr., vol. 118:7–18]. Both IGF species stimulate DNA, RNA, and protein synthesis and are involved in the proliferation, differentiation, and chemotaxis of some cell types. Local administration of IGF-I is known to stimulate the regeneration of peripheral nerves. In addition, IGF-I and PDGF, when administered topically to wounds in pigs, synergize to promote more effective healing than when either factor is administered alone [Skoffner et al., (1988) Acta. Paediatr. Scand. (Suppl), vol. 347:110–12].

Interferons were first identified as proteins that render cells resistant to infection from a wide range of viruses. Three Interferon types have been identified, α-IFN, β-IFN, and γ-IFN, which are produced by activated T and NK (natural killer) cells. α-IFN is comprised of a family of 15 or so closely related proteins while β-IFN and γ-IFN exist as single species. In addition, a synthetic consensus α-IFN, designed to incorporate regions of commonality among all known α-IFN subtypes, is disclosed in U.S. Pat. No. 4,897,471, hereby incorporated by reference. All IFNs are growth inhibitory molecules playing an important role in the lymphokine cascade. Each exerts a wide range of regulatory actions in normal cells, cancer cells, and host immune defense cells. γ-IFN's activities include macrophage activation for enhanced phagocytosis and tumor killing capacity. At present, these proteins are mainly used in cancer therapy [Balkhill et al., (1987) Lancet, pg: 317–18].

The Interleukins (ILs) are a polypeptide family playing a major role in the body's immune response. They are produced by many cell types, particularly T cells, in response to antigenic or mitogenic stimulation. IL-1 is produced following foreign antigen recognition. In addition to mediating the immune response IL-1 is involved in the inflammatory response to acute infection. IL-1 activates B cells and T cells. It induces IL-2 synthesis. It serves as a cofactor in B cell proliferation and differentiation. It enhances T cell and NK cell toxicity. IL-1 also enhances the response of bone marrow progenitors to various colony stimulating factors (CSFs). In inflammation, IL-1 causes bone marrow granulocyte release, serves as a polymononuclear cell chemoattractant, stimulates fibroblast proliferation, and plays a role in collagenase release [Genetically Engineered Human Therapeutic Drugs, Copsey and Delnatte, Stockton Press, 1988].

T cell synthesis of IL-2 is induced by IL-1. IL-2 is a B cell and T cell growth factor. It is also a NK cell growth and activation signal, stimulating them to become highly cytotoxic lymphokine activated killer (LAK) cells. IL-2 also regulates macrophage activity, promoting cytotoxicity [Genetically Engineered Human Therapeutic Drugs, supra]. IL-3, also called multi-CSF, synthesized by antigen or mitogen induced T lymphocytes, is involved in the growth and differentiation of hematopoietic progenitors [O'Garra, (1990) Lancet, vol 1: 1003–1005]. In vitro, IL-4 is essential for mucosal and connective tissue growth. It also enhances the tumoricidal activity and antigen presenting ability of macrophages. IL-4 synergistically interacts with CSFs on many non-terminally differentiated hematopoietic cell lineages. Further, it activates resting B cells [O'Garra, supra; The Atlas of Science, Kishimoto, ISI, 1988]. IL-4 also down regulates monocyte immune function, inhibiting monocyte and macrophage activity and suppressing IL-8 production in stimulated monocytes [Standiford et al., (1990) J. Immunol., vol. 145, No. 5: 1435–39].

After antigenic stimulation, IL-5 induces B cell growth and differentiation into immunoglobulin secreting cells [O'Garra, supra]. It also stimulates the proliferation, differentiation, and activation of eosinophils [Genetically Engineered Human Therapeutic Drugs, supra]. IL-6, produced by fibroblasts, endothelial cells, and monocytes, in addition to T cells, induces the terminal differentiation of activated B cells into antibody producing cells. Further, it activates hematopoietic progenitors to respond to IL-3 [Genetically Engineered Human Therapeutic Drugs, supra; The Atlas of Science, supra]. IL-7 induces in vitro B cell and thymocyte proliferation [O'Garra, supra]. IL-8 is expressed in both immune and non-immune cell types. In stimulated monocytes, IL-8 expression is suppressed by IL-4, while expression in fibroblasts and endothelial previously activated by tumor necrosis factor (TNF) or IL-1 is not suppressed by IL-4. In vivo, factors mediating neutrophil migration are unknown, but IL-8, having potent neutrophil activating and chemotactic activities, may mediate in vivo neutrophil accumulation [Standiford et al., (1990) Biochem. and Biophys. Res. Comm., vol. 171, No. 2: 531–36].

IL-9 is expressed in certain T cell lines and by mitogen stimulated peripheral blood lymphocytes [Yang et al., (1989) Blood, vol. 74, No. 6: 1880–84]. IL-9 enhances mast cell proliferation and it also stimulates IL-6 production in bone marrow-derived mast cells [Hultner et al., (1990) Exp. Hematol., vol. 18: 873–77]. Recently discovered in mice, IL-10, also called mouse cytokine synthesis inhibitory factor (CSIF), inhibits cytokine production in stimulated non-humoral T cell populations [Moore et al., (1990) Science, vol. 248: 1230–34].

KGF is an epithelial cell specific mitogen secreted by normal stromal fibroblasts. In vitro, it has been demonstrated to be as potent as EGF in stimulating the proliferation of human keratinocytes [Marchese et al., (1990) J. Cell Physiol., vol. 144, No. 2: 326–32].

M-CSF, also known as CSF-1, is a homodimeric colony stimulating factor which acts solely on macrophage progenitors. This macrophage lineage specific protein is produced constitutively in vitro by fibroblasts and stromal cell lines. In vivo, unlike other CSFs, M-CSF appears early in embryogenesis, suggesting a potential developmental role for this polypeptide [DeLamarter, J., (1988) Biochemical Pharmacology, vol. 37, No. 16: 3057–62].

PD-ECGF is a platelet derived endothelial cell mitogen having a molecular weight of approximately 45 kD. In contrast to the FGF family of endothelial cell mitogens, PD-ECGF does not bind heparin nor does it induce fibroblast proliferation. However, PD-ECGF does stimulate endothelial cell growth and chemotaxis in vitro and angiogenesis in vivo [Ishikawa et al., (1989) Nature, vol. 338: 557–61].

PDGF is a potent stimulator of mesenchymal cell types, like fibroblasts and smooth muscle cells, but it does not stimulate the growth of epithelial or endothelial cells [Ross et al., (1986) Cell, vol. 45: 155–69]. At low concentrations, PDGF acts as a chemoattractant for fibroblasts, and also as a chemoattractant and activating signal for monocytes and neutrophils [Deuel et al., (1982) J. Clin. Invest., vol. 69: 1046–49].

Recombinant SCF is a novel cellular growth factor which stimulates the growth of early hematopoietic progenitor cells, neural stem cells, and primordial germ stem cells [PCT/US90/05548, filed Sep. 28, 1990]. SCF exhibits potent synergistic activities in conjunction with colony stimulating factors, resulting in increased numbers of colonies and colonies of greater size [Martin et al., (1990) Cell, vol. 63: 203–11]. Thus, administration of SCF to mammals in pharmacologic doses, alone or in combination with other colony stimulating factors or other hematopoietic growth factors, may lead to the improvement of damaged cells in a number of divergent organ systems.

TGF-α and TGF-β act synergistically to induce anchorage independent growth in certain cancer cell lines. TGF-β is comprised of a class of disulfide linked homodimeric proteins, each chain being composed of 112 amino acids [Sporn et al., (1987) J. Cell Biol., vol. 105: 1039–45]. This dimeric protein produces many biological effects, such as mitogenesis, growth inhibition, and differentiation induction depending upon the assay used. TGF-β1 is the most studied TGF-β species in relation to wound healing [Ten Dijke, supra]. As a class, TGF-β is a potent monocyte and fibroblast chemoattractant.

Because each of these recombinant growth factors mentioned above may be capable of acting as a mitogen, inhibitor, or chemoattractant for the cell types heavily involved in the wound healing process, i.e. monocyte/macrophage, neutrophil, fibroblast, and endothelial and epithelial cells, they have been studied extensively in animal wound healing models. The most studied growth factor in relation to wound healing, EGF, has been found to accelerate the healing of surface wounds and burns when repeatedly applied to the wound site. PDGF and TGF-β increase the healing rate of incisional wounds when administered one time to the incision site shortly after the wound is made. However, no work describing the use of other factors, such as hematopoietic colony stimulating factors, can be found in the literature.

Thus, the object of the present invention is to provide a method for accelerating the wound healing process. Relating to wounds that will heal normally, the described method will accelerate this process. Concerning wounds that typically resist healing, this method will enable healing of these wounds as well. This method should reduce the time required for injury repair, and as such will lessen the time those burdened with injury will have to endure as their wounds heal.

SUMMARY OF THE INVENTION

The present invention provides for a method of promoting accelerated wound healing in an injured patient by administering a therapeutically effective amount of recombinant GM-CSF to the patient at the wounded area. This can be accomplished by incorporating the therapeutic agent into various materials, including: collagen based creams, films, microcapsules, or powders; hyaluronic acid or other glycosaminoglycan-derived preparations; creams, foams, suture material; and wound dressings. Alternatively, the therapeutic agent can be incorporated into a pharmaceutically acceptable solution designed for topical administration. Further, the therapeutic agent can be formulated for parenteral administration.

The methods of the present invention are effective in accelerating wound healing in incisional, compression, thermal, acute, chronic, infected, and sterile injuries.

Additionally, GM-CSF can also be incorporated into an admixture containing at least one of the following recombinant proteins: EGF, FGF, G-CSF, IGF-I, IGF-II, insulin, an Interferon, an Interleukin, KGF, M-CSF, PD-ECGF, PDGF, SCF, TGF-α, and TGF-β. These admixtures are also effective in promoting accelerated wound healing in injured patients.

Figure 1:
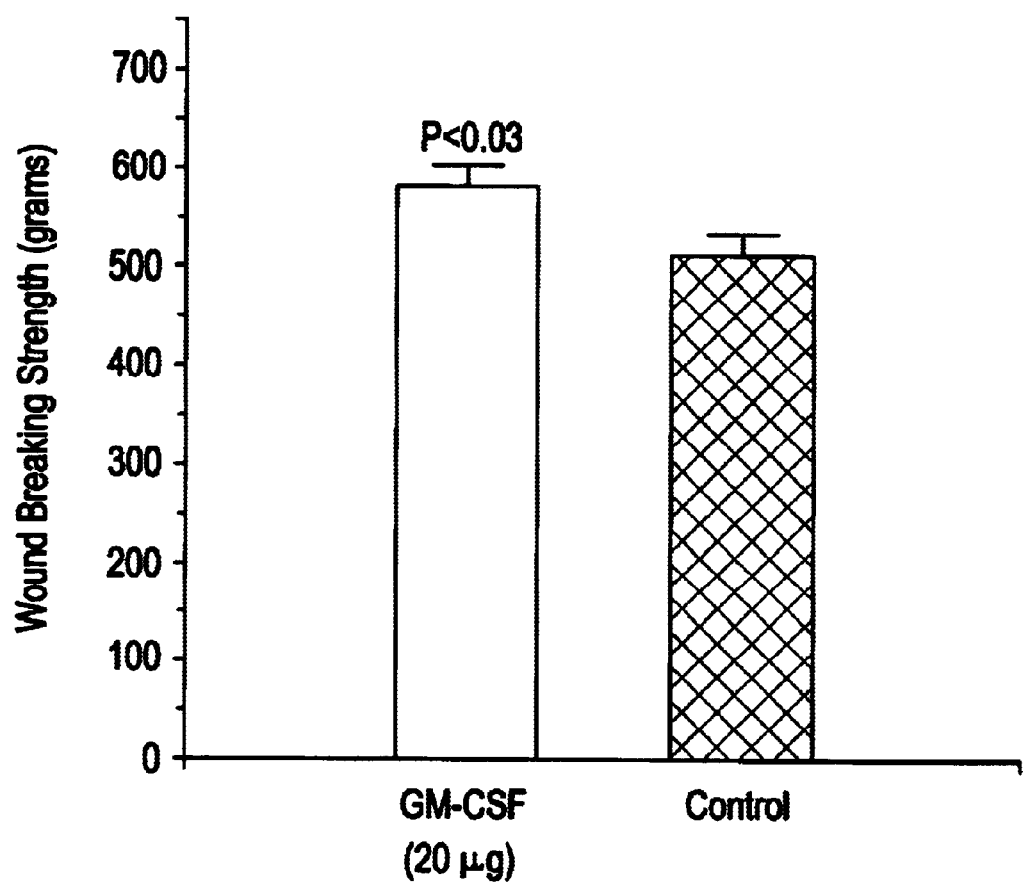
FIG. 1 depicts the breaking strength of incisional wounds treated with 20 μg of recombinant GM-CSF versus the breaking strength of similar wounds left to heal naturally.

Numerous aspects and advantages of the invention will be apparent to those skilled in the art upon consideration of the following detailed description which provides illumination of the practice of the invention in its preferred embodiments.

DETAILED DESCRIPTION

Because the typical wound is localized, cell types needed to effect wound repair must be concentrated in and around the injured area. Thus it is preferable that the factors necessary to promote the wound healing activity of these cell types be present in the afflicted area. Topical delivery of the polypeptide(s) is the most efficient way to achieve these goals.

The instant invention is based upon the discovery that recombinant GM-CSF can accelerate the wound healing process for all wound types, particularly when administered topically, i.e. to the surface of the wound site. so delivered, all wound types, mechanical or thermal, acute or chronic, infected or sterile, undergo healing more rapidly than similar wounds left to heal naturally or which are treated with currently available methods. However, as mentioned previously, parenteral administration of polypeptides having a role in the wound healing process is also envisioned by the present invention.

The wound healing process requires the formation of underlying connective tissue and reepithelialization after injury. A full thickness, surgically created rat incisional wound model was used to demonstrate the ability of recombinant GM-CSF to accelerate the wound healing process. This incisional rat model is analogous to full thickness incisional wounds in humans.

Additionally, a full thickness chronically granulating infected rat wound model was employed to simulate a typical chronic, non-healing human wound. In the rat model, significant bacterial contamination inhibits natural wound healing, perhaps by prolonging the inflammatory phase of the healing process. Daily administration of GM-CSF overcame this bacterial inhibition, despite the continued persistence of significant bacterial infection. Use of this chronically granulating infected wound model demonstrated that GM-CSF can promote wound healing in wounds typically resistant to repair.

In accordance with the present invention, the term "injury" shall be defined as a wound which extends from the surface of a patient's skin into the underlying tissue, and in fact the injury may pass completely through the patient, leaving both entrance and exit wounds. "Patient" refers to a mammal which has suffered an injury as defined above. "Therapeutic agent" means a compound that produces a therapeutically desirable result, such as accelerated wound healing. In the present invention, the therapeutic agent is GM-CSF and GM-CSF. Additionally, the term "therapeutic agent" refers to a combination of CSF combined with at least one of the following compounds: EGF, FGF, G-CSF, IGF-I, IGF-II, insulin, an Interferon, an Interleukin, KGF, M-CSF, PD-ECGF, PDGF, SCF, TGF-α, and TGF-β. Here, "accelerated wound healing" is defined as the process of wound healing which, as the result of the administration of a therapeutic agent in accordance with the present invention, occurs more rapidly than in a wound not receiving treatment with the therapeutic agent.

"Topical administration" shall be defined as the delivery of the therapeutic agent to the surface of the wound and adjacent epithelium. "Parenteral administration" is the systemic delivery of the therapeutic agent via injection to the patient. A "therapeutically effective amount" of a therapeutic agent within the meaning of the present invention will be determined by a patient's attending physician or veterinarian. Such amounts are readily ascertained by one of ordinary skill in the art and will enable accelerated wound healing when administered in accordance with the present invention. Factors which influence what a therapeutically effective amount will be include, the specific activity of the therapeutic agent being used, the wound type (mechanical or thermal, full or partial thickness, etc.), the size of the wound, the wound's depth (if full thickness), the absence or presence of infection, time elapsed since the injury's infliction, and the age, physical condition, existence of other disease states, and nutritional status of the patient. Additionally, other medication the patient may be receiving will effect the determination of the therapeutically effective amount of the therapeutic agent to administer. "Pharmaceutically acceptable" means that the components, in addition to the therapeutic agent, comprising the formulation are suitable for administration to the patient being treated in accordance with the present invention.

In accordance with the present invention, "wound dressings" are any of a variety of materials utilized for covering and protecting a wound. Examples include occlusive dressings, adhesive dressings, antiseptic dressings, and protective dressings. In pharmaceutical preparations, a "cream" is a semisolid emulsion of the oil-in-water or water-in-oil type suitable for topical administration. In accordance with the present invention, creams and foams used will also be suitable for use with the therapeutic agents herein described.

Recombinant GM-CSF, when administered as taught by the present invention in a therapeutically effective amount, significantly accelerates the wound healing process in all wound types. The mechanisms by which GM-CSF promotes acceleration of this process are believed to be associated with increased macrophage activity brought about by administration of this compound. In natural wound systems, extracellular growth factors such as GM-CSF may be present in rate limiting quantities. Thus, parenteral and/or topical administration of such factors may promote accelerated wound healing.

In vitro GM-CSF increases the proliferation of granulocytes and macrophages. In addition, this polypeptide increases the chemotaxis of these cells towards known chemoattractants. In vivo, administration of exogenous recombinant GM-CSF enhances an organism's ability to respond to injury. Increased chemotaxis promotes more rapid wound debridement, leading to a shorter inflammatory phase. Macrophages are heavily involved in the degradation of the clot which initiates the healing process, its replacement with granulation tissue, and the further maturation and remodeling of the reepithelialized wound. The presence of increased numbers of this cell type, in addition to enhanced cellular activity, help to lessen the time required for healing to occur. Additionally, macrophages themselves release factors which inhibit or stimulate other cell types, such as fibroblasts, which play important roles in wound healing.

In contrast, recombinant G-CSF stimulates the production and proliferation of predominantly neutrophilic cells. Although neutrophils are not an absolute requirement for wound healing, their presence in the inflammatory phase assists in a more rapid removal of devitalized tissue and other contaminants from the injury site. Chronic wounds, particularly those which are infected, resist healing by definition. These wounds typically remain in a persistent inflammatory phase. The administration of recombinant G-CSF, and consequent increased granulocyte activity, ingress, and local proliferation may enable the more rapid and complete removal of those elements responsible for prolonging the inflammatory phase, thus enabling the healing process to progress.

Any analogs of GM-CSF possessing comparable or enhanced in vivo biological activity can be used in accordance with the methods of the present invention. Such analogs may be generated by the deletion, insertion, or substitution of amino acids in the primary structure of the the naturally occurring proteins, or by chemical modification, such as by pegylation, of the protein. For example, to enable expression of these polypeptides in procaryotic host microorganisms, an initial methionine codon is required for translation initiation. Other analogs may have greater in vitro and/or in vivo biological activity, exhibit greater pH or temperature stability, maintain biological activity over a broader range of environmental conditions, or may have longer half-lives or clearance times in vivo.

To manufacture sufficient quantities of GM-CSF for commercial pharmaceutical application, these proteins are produced as the products of recombinant host cell expression. It is known that biologically active forms of GM-CSF can be recovered in large quantities from procaryotic hosts such as *E. coli* when such hosts, transformed with appropriate expression vectors encoding these polypeptides, are grown under conditions allowing expression of the exogenous gene. It is therefore preferred to utilize GM-CSF produced in this manner.

The recombinant GM-CSF is formulated into a pharmaceutical formulation suitable for patient administration. As will be appreciated by those skilled in the art, such formulations may include pharmaceutically acceptable adjuvants and diluents. When administered systemically, a therapeutically effective amount of the therapeutic agent is delivered by the parenteral route, i.e. by subcutaneous, intravenous, intramuscular, or intraperitoneal injection. Wound treatment by parenteral injection may involve either single, multiple, or continuous administration of the therapeutic agent, depending upon various factors, including the injury type, severity, and location.

In a preferred embodiment of the present invention, recombinant GM-CSF should be topically administered to the wound site to promote accelerated wound healing in the patient. This topical administration can be as a single dose or as repeated doses given at multiple designated intervals. It will readily be appreciated by those skilled in the art that the preferred dosage regimen will vary with the type and severity of the injury being treated. For example, surgical incisional wounds cause little damage to surrounding tissues, as little energy is transmitted to the tissues from the object inflicting the injury. It has been found that a single topical administration of the therapeutic agent results in significantly more rapid healing than in identical wounds which go untreated. Where the wound is infected and chronically granulating, repeated daily application of the therapeutic agent has been found to produce more rapid wound healing than in similar wounds receiving no treatment.

While it is possible to administer the therapeutic agent as a pure or substantially pure compound, i.e. not incorporated into any pharmaceutical formulation, it is preferable instead to present the therapeutic agent in a pharmaceutical formulation or composition. Such formulations comprise a therapeutically effective amount of the therapeutic agent with one or more pharmaceutically acceptable carriers and/or adjuvants. The carriers employed must be compatible with the other ingredients in the formulation. Preferably, the formulation will not include oxidizing or reducing agents or other substances known to be incompatible with the described polypeptides. All formulation methods include the step of bringing the biologically active ingredient into association with the carrier(s) and/or adjuvant(s). In general, the therapeutic agent of the instant invention will be formulated by bringing the agent into association with liquid carriers, finely divided solid carriers, or both.

Formulations suitable for topical administration in accordance with the present invention comprise therapeutically effective amounts of the therapeutic agent with one or more pharmaceutically acceptable carriers and/or adjuvants. An aqueous or collagen-based carrier vehicle is preferred for topical administration of the therapeutic agents described by the present invention. When the formulation is to be administered but one time, a collagen-based carrier vehicle is preferred. An example of such a vehicle is Zyderm® (Collagen Corp., Palo Alto, Calif.). If the wound being treated requires multiple applications of the therapeutic agent at designated intervals, it is preferred to utilize a pharmaceutically acceptable aqueous vehicle for delivery. However, it is also possible to incorporate the therapeutic agent into a variety of materials routinely used in the treatment of wounds. Such materials include hyaluronic acid or other glycosaminoglycan-derived preparations, sutures, and wound dressings.

When the therapeutic agent used in accordance with the present invention is comprised of more than one protein, the resultant admixture is administered in the same fashion as formulations comprising only one polypeptide as the therapeutic agent.

The following examples are offered to more fully illustrate the present invention, but are not meant to limit the scope thereof.

EXAMPLE 1

Full Thickness Incisional Model

Eight young adult male Sprague-Dawley rats weighing 300–350 grams (Sasco; Omaha, NE) were anesthetized with pentobarbital. The back of each animal was shaved and scrubbed. In a sterile field, two 6 cm full thickness incisions were made on the back of each rat. Each incision was 1.5 cm from the dorsal midline. A bovine collagen suspension containing 1 mg collagen and 20 $\mu$g GM-CSF was then administered into the length of one of the two wounds in each animal using a tuberculin syringe. A suspension containing bovine collagen only was then injected into the other wound in each animal to serve as an internal control. The wounds were then coapted with three evenly spaced surgical clips. After surgery, the animals were kept 10 days in single cages, at which point they were removed for harvesting.

The harvest was conducted by first humanely sacrificing each rat. After sacrifice, the entire dorsal skin region was carefully removed surgically. A template with parallel surgical blades was then used to remove two or three strips of skin from the area spanning each wound and perpendicular to the incisional axis. Each strip was 8 mm in width and was excised from the region between the surgical clips. After excision, matched and paired samples from the experimental and control wounds were kept moistened and were then used to determine the breaking strength of GM-CSF treated and untreated wounds. In addition, one or two samples from the end of each incision were also excised and fixed for histological analysis.

A tensometer (Tensometer 10; Monsanto Co., St. Louis, Mo.) was utilized to determine the breaking strength of the coapted wounds. FIG. 1 depicts the results of the breaking strength measurements. Measurements were not performed on wounds showing any evidence of infection, excessive hemorrhage, or poor coaptation. Paired t-tests of breaking strength scores and differences between experimental and control values were performed using the SAS data analysis system (Division of Biostatistics, Washington University, St. Louis, Mo.). These analyses revealed a t-test value of 2.136298 and a p-value of 0.038, indicating that GM-CSF treatment significantly enhances the breaking strength of healing wounds compared to untreated controls.

Histological analysis of the coapted wounds was conducted by examining the samples removed from the ends of the incisions 24–48 hours after excision. Prior to examination, each sample was embedded in paraffin and sliced into thin sections 3 $\mu$m thick. Sections to be examined for cellularity and granulation tissue formation were stained with hematoxylin and counterstained with eosin by standard techniques. These sections were then scored by light microscopy at 100× by two independent observers. These observations showed that GM-CSF treated wounds had undergone a much greater influx of monocytes and fibroblasts than untreated wounds.

These tensometry and histology results indicate that a single treatment with 20 $\mu$g GM-CSF significantly accelerates the wound healing process in vivo. Increased cellularity and collagen production were observed in GM-CSF treated wounds as compared to untreated control wounds. Thus, the increase in breaking strength observed in GM-CSF treated wounds can be attributed to the ability of topically administered GM-CSF to promote a greater ingress of macrophages and fibroblasts into wounded areas. This rapid increase in cellularity in turn leads to an earlier transition from granulation tissue to the collagen-based matrix characteristic of scar tissue.

In addition to the experiment described above, another experiment utilizing the same full thickness incisional wound model was also conducted to compare topical versus systemic GM-CSF treatment. Here, male Sprague-Dawley rats, weighing 250–300 g, were used. Full thickness incisions were prepared as described above. For topical administration, recombinant GM-CSF (0.5 mg/ml) was combined with an emulsified bovine collagen suspension (10 mg/ml) such that 30 µg of GM-CSF was applied to each wound cleft at the time of closure using a tuberculin syringe in a total volume of 0.1 ml. The paired control wound in each animal received 100 µl of the collagen vehicle only.

A separate series of animals was established to examine the effect of topical GM-CSF administration on incisional wounds in monocytopenic animals. Monocytopenia was induced by giving each experimental animal an intramuscular injection of 30 mg/kg (about 10 mg/rat) of methylprednisolone two days prior to wounding. Tail-vein complete blood counts were taken two days post-wounding from a representative set of animals from each group (both normal and monocytopenic) in order to examine the possible systemic effects of topical GM-CSF administration to the wound site. These counts, particularly the white blood cell differential, revealed a lack of significant systemic absorption of GM-CSF when it is topically administered.

The topically treated animals were sacrificed at either day 7 or day 14 post-wounding. Their pelts were subsequently harvested and three standardized 8 mm strips were obtained from each wound site as described previously. Each of these strips was then subjected to a breaking strength analysis using a tensometer. Results were analyzed using the paired Student's t-test (Basica, IBM Corp.). All wounds showing excessive scabbing or poor approximation (<5% of all wounds) were excluded from the analysis. The results for the normal, i.e., non-monocytopenic, animals appear in FIG. 2 and confirm the results depicted in FIG. 1, namely that topical administration of GM-CSF to an incisional wound significantly increases the rate of wound healing. Contrary results were obtained with respect to the monocytopenic rats. The glucocorticoid treatment prior to wounding eliminated the positive effect of topical GM-CSF administration to the wound site.

Conducted simultaneously with the above topical administration experiments, GM-CSF was also given systemically to rats which had received identical incisional wounds. These animals were injected subcutaneously with 100 µg/kg of GM-CSF in a phosphate buffer vehicle every 12 hours, beginning two days prior to wounding and continuing for five days after the incisions were made. Control animals received injections of equivalent volumes of saline alone on the same schedule. Tail vein blood samples were drawn the day before and on days one and nine after GM-CSF administration began. These animals were humanely sacrificed seven days after surgery and wound breaking strengths were measured as described above. The results obtained for the incisionally wounded animals treated systemically with GM-CSF revealed that such a delivery route, for GM-CSF to be effective in promoting accelerated healing in incisional wounds, is ineffective. Although the blood cell analysis showed a definite response to GM-CSF administration, the wounds on animals receiving GM-CSF subcutaneously showed no greater breaking strength than those from saline-treated animals. The results, when coupled with those presented above for topical administration, clearly show application of GM-CSF to the wound itself to be the most effective method for accelerating healing in wounded animals.

EXAMPLE 2
Chronically Granulating Wound Model 72 male Sprague-Dawley rats (Sasco; Omaha, Nebr.) weighing 200–250 grams were anesthetized and the dorsal surface of each rat was then shaved and disinfected. Each rat then received a modified Brooke Burn Model injury comprised of a 20% full thickness scald burn on its dorsal surface. The modified Brooke Burn Model [Walker et al., (1964), Annals of Surgery, August: 297–305] employed utilized a template which was heated to 100° C. This template was then placed on the back of the experimental animal for 15 seconds. Immediately following the infliction of the burn, $10^8$ E. coli (ATCC strain 25922) were inoculated evenly over the scalded wound in 40 of the rats. After recovering from the anesthetic, the animals were placed in a single cage housing.

Five days after the wounds were inflicted, those animals surviving the burn wound infection underwent escharectomy under anesthesia, whereby the eschar covering the wound was removed by mechanical means. Removal of the eschar established the chronically granulating wound with tissue bacterial levels in the range of $10^5$ bacteria/gram tissue. Quantitative and qualitative bacterial analysis was conducted by first cleansing the wound with isopropyl alcohol after eschar removal. A biopsy was then obtained by removing a 2–3 mm core of granulation tissue. The biopsy was then weighed, flamed, homogenized, and diluted in a solution containing 1:10 thioglycollate. Serial dilutions of this solution were then made and backplated onto blood agar plates to arrive at a bacterial count.

After the initial bacterial counts had been established, the animals were divided into three groups. Group 1 consisted of 20 animals which had not been infected with E. coli, received no GM-CSF treatment, and were designated the untreated control group. Groups 2 and 3 constituted the experimental groups. Group 2, consisting of 20 animals, received topically administered inert vehicle only according to the same schedule as Group 3, which received 10 µg GM-CSF per administration. In Groups 2 and 3, the appropriate topical formulations were delivered with a tuberculin syringe daily for 10 days. The rate of epithelialization and/or wound contraction was determined by radial planimetry every 2 to 3 days during the course of the experiment. In addition, biopsies were obtained on days 5 and 10 to determine the bacterial levels in the wounds of the various groups. Tissue bacterial counts were lower in Group 3 (mean=$3.78 \times 10^5$ bacteria/g) than in the infected control (Group 2, mean=$1.9 \times 10^7$) on day 10. However, the bacterial levels in both Groups 2 and 3 remained significantly higher than those in Group 1 (mean<$10^2$ bacteria/g) throughout the course of the experiment.

Figure 2:
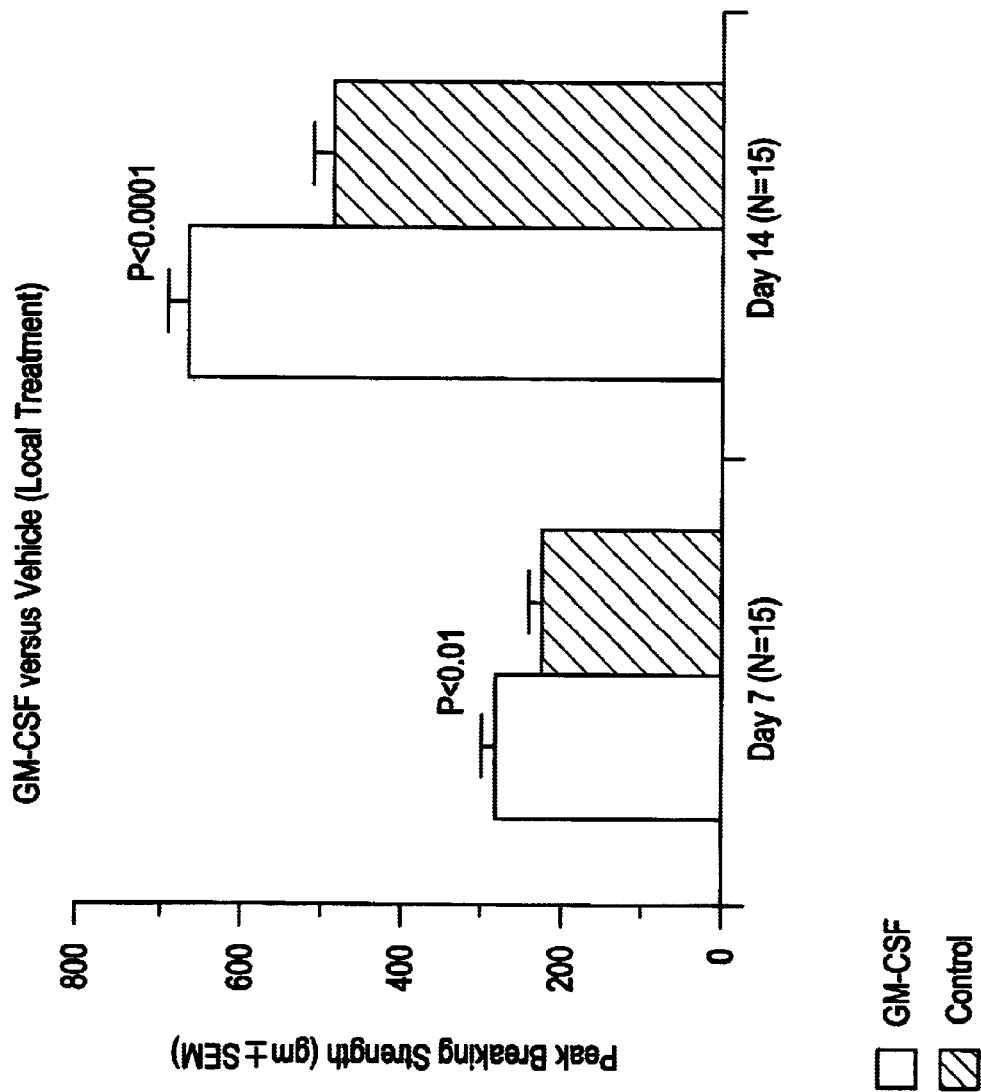
FIG. 2 depicts the breaking strength at days 7 and 14 post-wounding of incisional wounds that have been treated topically with 30 μg of GM-CSF.
Figure 3:
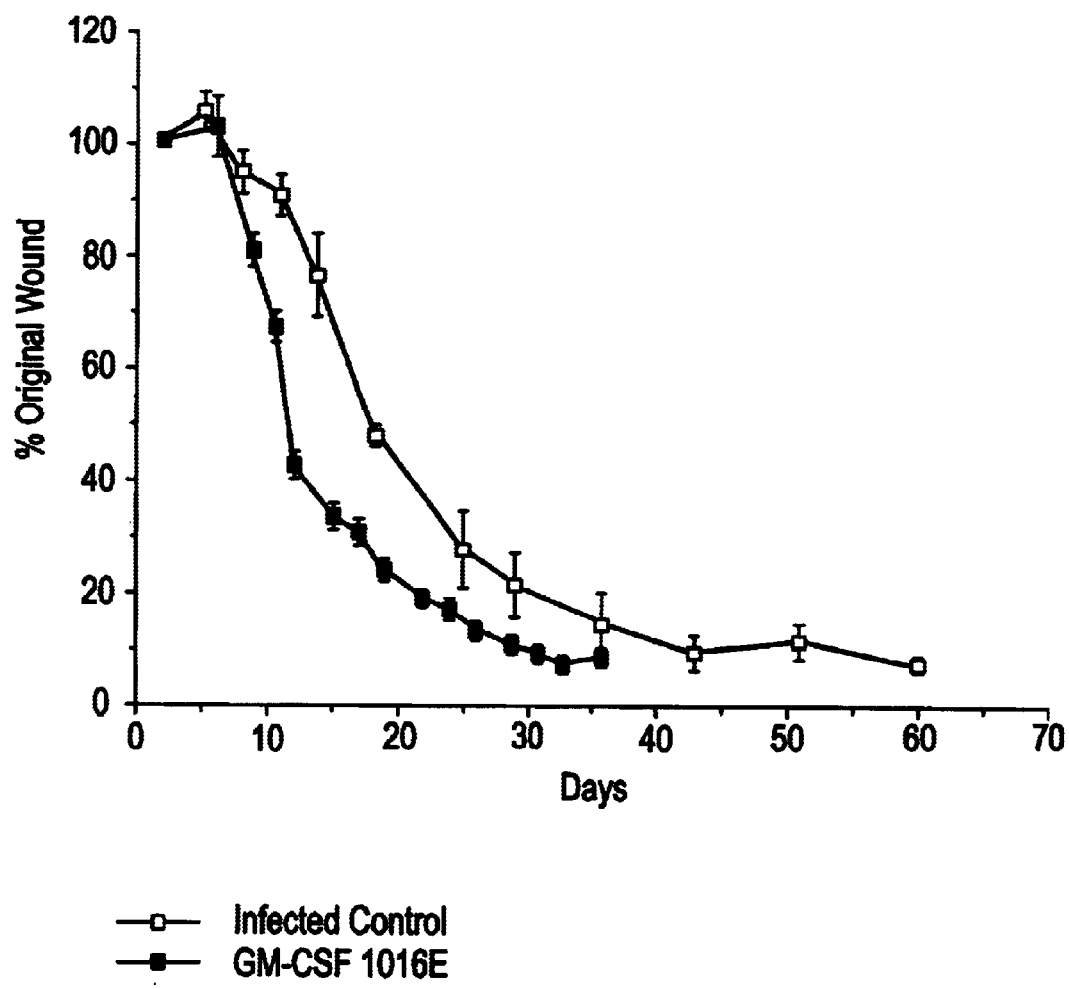
FIG. 3 depicts the rate of wound closure in untreated and recombinant GM-CSF treated chronically granulating infected wounds.

The chronically granulating wounds of Group 2 healed more slowly than the wounds in the animals of Group 1, establishing that bacterial contamination inhibits wound healing in this model. However, the GM-CSF treated animals in Group 3 were able to overcome this bacterial inhibition, as is evidenced by the significantly faster wound healing ($p \leq 0.005$ Wilcoxon) than was observed in Group 2 (FIG. 2). Thus, topical application of GM-CSF accelerates wound closure despite continued heavy bacterial contamination. In fact, the rate of wound closure obtained in the chronically granulating wound upon GM-CSF administration approached that observed in the non-infected animals. These results indicate that the topical application of GM-CSF to wounds previously incapable of healing allows a normal rate of wound healing to be obtained, even in highly contaminated wounds.

While the present invention has been described in terms of preferred embodiments, it is understood that variations and modifications will occur to those skilled in the art in light of the above description. Therefore, it is intended that the appended claims cover all such variations which come within the scope of the invention as claimed.

What is claimed is:

1. A method for promoting accelerated wound healing in an injured patient comprising topical administration to the patient of 40–67 μg/kg granulocyte macrophage-colony stimulating factor (GM-CSF).

2. A method according to claim 1 wherein the GM-CSF is the product of eukaryotic host cell expression.

3. A method according to claim 1 wherein the GM-CSF is expressed in a procaryotic host cell.

4. A method according to claim 1 wherein the injury is the type selected from the group consisting of mechanical, thermal, acute, chronic, infected, and sterile wounds.

5. A method according to claim 1 wherein the injured patient is a human.

6. A method according to claim 3 wherein the procaryotic host cell is *E. coli*.

7. A method according to claim 6 wherein the GM-CSF is human GM-CSF.

8. A method according to claim 1 further comprising administering at least one other recombinant protein selected from the group consisting of EGF, FGF, KGF, PD-ECGF, PDGF, TGF-α, and TGF-β.

9. A method according to claim 1 wherein topical administration of a pharmaceutically acceptable formulation comprising 40–67 μg/kg of GM-CSF is conducted through the application of a GM-CSF comprising wound covering selected from the group consisting of a collagen based cream, a collagen based film, a collagen based microcapsule, a collagen based powder, hyaluronic acid or other glycosaminoglycans, creams, foams, suture material, and wound dressing.

10. A method according to claim 9 further comprising administering at least one other protein selected from the group consisting of EGF, FGF, KGF, PD-ECGF, PDGF, TGF-α, and TGF-β.

11. A method according to claim 1 wherein topical administration of a pharmaceutically acceptable formulation comprising 40–67 μg/kg of GM-CSF is conducted through the application of a solution comprising GM-CSF.

12. A method according to claim 11 further comprising administering at least one other protein selected from the group consisting of EGF, FGF, KGF, PD-ECGF, PDGF, TGF-α and TGF-β.

* * * * *

UNITED STATES PATENT AND TRADEMARK OFFICE
CERTIFICATE OF CORRECTION

PATENT NO. : 6,689,351 B1 Page 1 of 1
DATED : February 10, 2004
INVENTOR(S) : Pierce et al.

It is certified that error appears in the above-identified patent and that said Letters Patent is hereby corrected as shown below:

Column 10,
Line 48, change "so delivered," to read -- When GM-CSF is so delivered, --.

Column 11,
Line 16, delete the duplicate phrase "and GM-CSF" after -- GM-CSF --.
Line 17, change "CSF" to read -- GM-CSF --.

Signed and Sealed this

Fourth Day of May, 2004

JON W. DUDAS
*Acting Director of the United States Patent and Trademark Office*